US010709809B2

(12) United States Patent
Heymans et al.

(10) Patent No.: US 10,709,809 B2
(45) Date of Patent: Jul. 14, 2020

(54) MULTI-LAYER ADHESIVE TAPE TO COMPRESS AND CONTRACT A SCAR

(71) Applicant: Michel Heymans, Grez Doiceau (BE)

(72) Inventors: Michel Heymans, Grez Doiceau (BE); Audrey Boelen, Bouffioulx (BE); Régis Barbieux, Braine le Comte (BE)

(73) Assignee: Michel Heymans, Grez Doiceau (BE)

( * ) Notice: Subject to any disclaimer, the term of this patent is extended or adjusted under 35 U.S.C. 154(b) by 355 days.

(21) Appl. No.: 15/540,848

(22) PCT Filed: Dec. 30, 2015

(86) PCT No.: PCT/EP2015/081404
§ 371 (c)(1),
(2) Date: Jun. 29, 2017

(87) PCT Pub. No.: WO2016/107897
PCT Pub. Date: Jul. 7, 2016

(65) Prior Publication Data
US 2017/0360984 A1 Dec. 21, 2017

(30) Foreign Application Priority Data

Dec. 30, 2014 (BE) .................................. 2014/5162
May 8, 2015 (BE) .................................. 2015/5293

(51) Int. Cl.
*A61F 13/02* (2006.01)
*A61L 15/58* (2006.01)
(Continued)

(52) U.S. Cl.
CPC .......... *A61L 15/58* (2013.01); *A61F 13/0243* (2013.01); *A61F 13/0253* (2013.01);
(Continued)

(58) Field of Classification Search
CPC .. A61K 9/7084; A61K 9/0014; A61K 9/7053; A61K 9/7061; A61K 9/7069;
(Continued)

(56) References Cited

U.S. PATENT DOCUMENTS 4,810,523 A * 3/1989 Williams ................... C08F 2/54
427/208.4
5,018,515 A * 5/1991 Gilman ............... A61F 13/0276
602/45
(Continued)

FOREIGN PATENT DOCUMENTS

CN       103002844      3/2013
WO       2011/159623    12/2011
(Continued)

OTHER PUBLICATIONS

International Search Report dated Mar. 8, 2016 in corresponding International (PCT) Application No. PCT/EP2015/081404.
(Continued)

*Primary Examiner* — Ophelia A Hawthorne
(74) *Attorney, Agent, or Firm* — Wenderoth, Lind & Ponack, L.L.P.

(57) ABSTRACT

A multi-layer adhesive tape to compress and contract one or more scars includes: a top layer; a bonding layer adjacent to the top layer; a bottom layer adjacent to the bonding layer and opposite to the top layer; an adhesive layer adjacent to the flexible bottom layer and opposite to the bonding layer; and a first peelable liner at least adjacent to the adhesive layer and opposite to the bottom layer. The widths of the top layer and bonding layer are larger than the widths of the bottom layer and adhesive layer, and the adhesive layer includes a rubber- or acrylic-based pressure-sensitive adhesive. Furthermore, the top layer can have a thickness between 20 μm and 1100 μm.

24 Claims, 2 Drawing Sheets

(51) Int. Cl.
*A61L 15/22* (2006.01)
*A61L 15/42* (2006.01)

(52) U.S. Cl.
CPC ........ *A61F 13/0259* (2013.01); *A61L 15/225* (2013.01); *A61L 15/42* (2013.01); *A61L 2420/08* (2013.01)

(58) Field of Classification Search
CPC ........ A61K 41/00; A61K 47/34; A61K 9/703; A61M 35/00; A61L 15/58; A61L 15/42; A61L 15/225; A61L 2420/08; A61F 13/0259; A61F 13/0253; A61F 13/0243
See application file for complete search history.

(56) References Cited

U.S. PATENT DOCUMENTS

| | | | |
|---|---|---|---|
| 5,656,279 | A | 8/1997 | Dillon |
| 5,662,925 | A * | 9/1997 | Ebert ............ A61K 9/703 424/447 |
| 5,780,048 | A | 7/1998 | Lee |
| 7,115,792 | B2 | 10/2006 | Kartheus et al. |
| 8,183,428 | B2 | 5/2012 | Gurtner et al. |
| 2004/0092855 | A1 | 5/2004 | Fabo |
| 2005/0177086 | A1* | 8/2005 | Murata ............ A61F 13/0203 602/41 |

FOREIGN PATENT DOCUMENTS

| | | |
|---|---|---|
| WO | 2012/092306 | 7/2012 |
| WO | 2014/091007 | 6/2014 |

OTHER PUBLICATIONS

Written Opinion of the International Searching Authority dated Mar. 8, 2016 in corresponding International (PCT) Application No. PCT/EP2015/081404.

3M, "Double Coated Tapes with Adhesive 300MP"; pp. 1-4; Oct. 2006.

* cited by examiner

MULTI-LAYER ADHESIVE TAPE TO COMPRESS AND CONTRACT A SCAR

TECHNICAL FIELD

The present invention relates to a multi-layer adhesive tape to compress and contract a scar.

BACKGROUND

Document U.S. Pat. No. 5,780,048 discloses a multi-layer tape which provides an airtight and watertight barrier to facilitate the process of healing of an open wound and prevent any contamination of the wound by the surrounding environment. The tape comprises four layers arranged successively as follows:

the first layer is designed to be placed on an open wound and is cyanoacrylate-based,
the second layer is made of flexible material,
the third layer is an adhesive layer, and
the fourth layer is a bandage based on an ethylene polymer blend.

The first and second layers have roughly the same width, which is smaller than that of the third and fourth layers. The third and fourth layers thus cover the first and second layers over their entire width.

A peelable covering may advantageously be placed on the first layer of the tape. The bandage is maintained in a vacuum or airtight system so as to prevent premature reaction between the components forming the tape.

During use, the bandage is taken out of its system and the peelable covering can be removed to be applied on a wound.

When the wound is closed, it is known that it may form a scar whose shape may change over time, which represents a problem for the user from an aesthetic point of view.

The state-of-the-art multi-layer tape is thus limited to treating open wounds and isolating them from their surrounding environment to reduce risks of contamination.

However, once the wound is closed, a scar remains visible to the naked eye and cannot be attenuated by the disclosed bandage. Consequently, once the wound is closed, this type of tape no longer suffices to reduce the visibility of the scar.

The purpose of the invention is to remedy the drawbacks of the state of the art by providing a multi-layer adhesive tape capable of attenuating the visibility of a scar.

SUMMARY OF THE INVENTION

A multi-layer adhesive tape to compress and contract one or more scars includes:
a top layer 4;
a bonding layer 3 adjacent to (adjoining) the top layer 4;
a bottom layer 2 adjacent to the bonding layer 3 and opposite to the top layer 4;
an adhesive layer 1 adjacent to the flexible bottom layer 2 and opposite to the bonding layer 3; and
a first peelable liner 7 at least adjacent to the adhesive layer 1 and opposite to the bottom layer 2. The widths L' of the top layer 4 and the bonding layer 3 are larger than the widths L of the bottom layer 2 and the adhesive layer 1, and the adhesive layer 1 comprises a rubber- or acrylic-based pressure-sensitive adhesive.

The adhesive layer 1 comprising rubber- or acrylic-based pressure-sensitive adhesive can easily be attached to one or more scars on the skin 5 of a user by the mere application of pressure, avoiding the need for solvent, water, or heat for activation of adhesive. This both facilitates the attachment of the multi-layer adhesive tape and ameliorates a standard hygienic use of such multi-layer adhesive tape.

A second aspect of the present invention provides a multi-layer adhesive tape to compress and contract a scar, the tape including:
a flexible top layer 4,
a bonding layer 3,
a flexible bottom layer 2 which includes an adhesive layer 1 which is designed to cover the scar. The bottom layer 2 and the top layer 4 are bound to each other by the bonding layer 3, and
the top layer 4 has a width greater than that of the bottom layer 2 so as to cover it over its entire width.

The top layer 4 has a thickness h between 20 µm and 1100 µm, preferably between 20 µm and 900 µm, more preferably between 20 µm and 800 µm, advantageously between 20 µm and 200 µm, even more advantageously between 50 µm and 100 µm, so as to obtain, in the position of application of the adhesive tape on the scar, a positive pressure P which is defined by the force applied by the top layer 4 on the surface of the scar 6, in accordance with the following pressure equation:

$$P = \frac{\varepsilon \cdot E \cdot h \cdot \sin\alpha}{L}$$

where,
P corresponds to the pressure applied by the tape on the scar 6,
$\varepsilon$ corresponds to the relative deformation of the top layer 4 and,
E represents the Young's modulus of the top layer 4,
h represents the thickness of the top layer 4,
L represents the width of the bottom layer 2, and
the angle $\alpha$ is defined between one of the ends of the top layer 4 and the surface of the scar 6.

Hence, it was noted surprisingly that the selection of a thickness between 20 µm and 1100 µm, preferably between 20 µm and 900 µm, more preferably between 20 µm and 800 µm, advantageously between 20 µm and 200 µm, even more advantageously between 50 µm and 100 µm for the top layer enables a "positive" pressure to be obtained directly on and around the scar. This has the effect of mechanically compressing and contracting the scar which enables the visibility of the scar to be reduced in an unexpected way.

DESCRIPTION OF FIGURES

In the figures, identical or similar elements carry the same references.

DETAILED DESCRIPTION OF THE INVENTION

Figure 1:
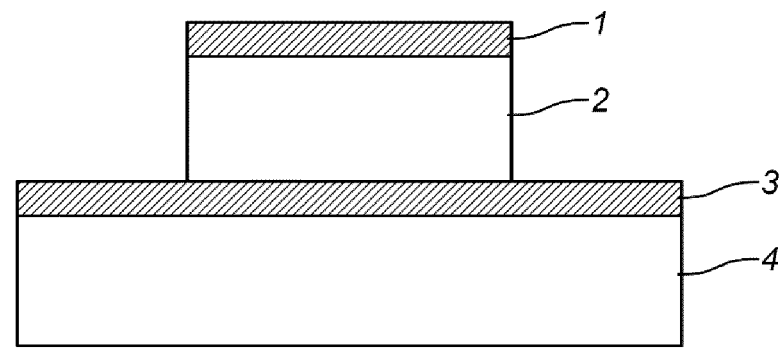
FIG. 1 illustrates the structure of the multi-layer tape according to the invention.

As used herein, the following terms have the following meanings:

The term "hot-melt adhesive" generally refers to a class of adhesives which are supplied as a solid at room temperature and flow upon heating to allow application to one or more substrate(s). Upon cooling the adhesive regains a solid form and moisture cures to bond to the substrate(s).

The term "polyolefin compounds" refers to any polymerized olefin, which can be linear, branched, cyclic, aliphatic, aromatic, substituted, or unsubstituted. More specifically, included in the term "polyolefin compounds" are homopolymers of olefin, copolymers of olefin, co-polymers of an olefin and a non-olefinic comonomer co-polymerizable with the olefin, such as vinyl monomers, modified polymers thereof, and the like. Specific examples include polyethylene homopolymer, polypropylene homopolymer, polybutene homo-polymer, ethylene alpha-olefin copolymer, propylene alpha-olefin copolymer, butene alpha-olefin copolymer, ethylene unsaturated ester copolymer, ethylene unsaturated acid co polymer, (e.g., ethylene ethyl acrylate copolymer, ethylene butyl acrylate copolymer, ethylene methyl acrylate copolymer, ethylene acrylic acid copolymer, and ethylene methacrylic acid copolymer), ethylene vinyl acetate copolymer, ionomer resin, polymethylpentene, etc.

The term "silicone material" refers to refers to any viscous composition having a polymerized siloxane, or polysiloxane. Polysiloxanes have a silicon-oxygen backbone (Si—O—Si—O—Si—O—) and an organic group (such as methyl, ethyl or phenyl) attached. The silicone material may be, for example, a linear silicone oil of the non-crosslinked polydimethylsiloxane type. Alternatively, the silicone material may be, for example, of the crosslinked organosiloxane type. The silicone material may be in the form of an emulsion. Suitable emulsions include but are not limited to water-in-silicone emulsions, oil-in-water emulsions, and silicone-in-water emulsions. Blends of one or more silicone materials with another component are also feasible, such as blends of one or more silicone materials with polytetrafluoroethylene.

The term "polyurethane" refers to polymeric or oligomeric materials comprising urethane groups, urea groups, or both. It should be clear that the term "polyurethane", as used herein, is not limited to those polymers which include only urethane or polyurethane linkages. It is well understood by those of ordinary skill in the art of preparing polyurethanes that the polyurethane polymers may also include allophanate, carbodiimide, uretidinedione, and other linkages in addition to urethane linkages.

The term "filmic material" refers to a plastic material in a thin layer. Non-limiting examples of plastic materials that can act as film material are polyolefins such as polypropylene and polyethylene; polyesters; polyamides; polyurethanes; polyvinylhalides such as polyvinylchloride; acetates; biopolymers, including cellulose and cellulosic derivatives, polylactic acid and polyhydroxy acid; and compatible mixtures, blends or copolymers of two or more thereof.

The term "UV blocking agents" refers to agents that block UV rays or UV radiation. The UV blocking agents are preferably inorganic, organic or metallic. Examples of such agents include, but are not limited to; muscovite, phlogopite, biotite, sericite, fushitite, margarite, synthetic mica, metal oxide coated mica, coloured pigment coated mica, talc, benzotriazole e.g chlorobenzotriazoles, para-aminobenzoic acid, metal oxides, metallic hydroxides, mixed metal oxides and hydroxides, metal and mixed metal silicates and aluminosilicates, transition metal oxides and hydroxides, $TiO_2$, $ZrO_2$, $Fe_2O_3$, natural clay, metal sulfides, non-metallic elements, ionic salts and covalent salts, powered ceramics, organic polymers, natural polymers, insoluble organic materials and biomaterials, particularly UV absorbing molecules, aluminium, copper, copper-bronze, bronze-gold, silver and collagen. In preferred embodiments, said UV blocking agents comprise one or more particles.

A first aspect of the present invention provides a multi-layer adhesive tape to compress and contract one or more scars. The adhesive tape includes a top layer 4; a bonding layer 3 adjacent to (adjoining) the top layer 4; a bottom layer 2 adjacent to the bonding layer 3 and opposite to the top layer 4; an adhesive layer 1 adjacent to the flexible bottom layer 2 and opposite to the bonding layer 3; and a first peelable liner 7 at least adjacent to the adhesive layer 1 and opposite to the bottom layer 2. The widths L' of the top layer 4 and bonding layer 3 are larger than the widths L of the bottom layer 2 and adhesive layer 1, and the adhesive layer 1 comprises a rubber- or acrylic-based pressure-sensitive adhesive.

Figure 3:
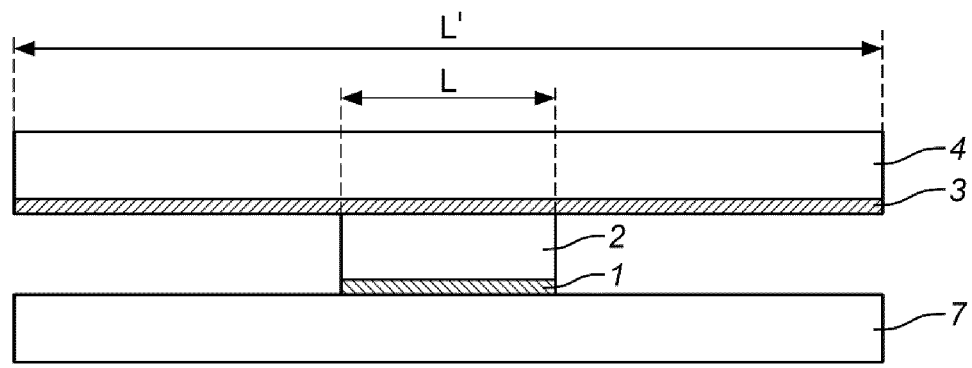
FIG. 3 is a schematic presentation of a preferred embodiment of the multi-layer adhesive tape according to the present invention.

The tape according to the first aspect of the present invention is ideally suited to compress and contract one or more scars on the skin 5 of a user. Therefore, the first peelable liner 7, which preferably shields both adhesive layer 1 and bonding layer 3, is first removed. Subsequently, the bottom layer 2 is brought into contact with the area of one or more scars 6 on the skin 5. The widths L' of the top layer 4 and the bonding layer 3 which are larger than the widths L of the bottom layer 2 and the adhesive layer 1 enable the bottom layer 2 to be pressed towards the skin 5, by applying parts of the bonding layer 3 to both the bottom layer 2 and the skin 5. In preferred embodiments, the top layer 4 and bonding layer are stretched while being applied on both skin 5 and bonding layer 3. The thus pressed bottom layer 2 exerts both a pressure on the one or more scars and affects a temperature rise on the one or more scars. These two physical actions have a pronounced effect upon the natural reorganization of the tissue of the one or more scars: the activity of collagenase, a key enzyme for the remodelling process, is increased, microcirculation in the one or more scars is activated, and an improved blood flow is achieved. A schematic presentation of a preferred embodiment of the multi-layer adhesive tape according to the first aspect of the present invention is shown in FIG. 3.

The adhesive layer 1 comprising rubber- or acrylic-based pressure-sensitive adhesive can easily be attached to one or more scars on the skin 5 of a user by the mere application of pressure, avoiding the need for solvent, water, or heat for activation of the adhesive. This both facilitates the attachment of the multi-layer adhesive tape and ameliorates a standard hygienic use of such multi-layer adhesive tape. The selection of a rubber- or acrylic-based pressure-sensitive adhesive for the adhesive layer 1 is not to be regarded as obvious by a person skilled in the art, since such person would rather select a more classical approach comprising the use of an adhesive which needs a solvent, water or heat for activation of the adhesive.

In preferred embodiments, the rubber- or acrylic-based pressure-sensitive adhesive is solvent- or water-based and/or a hot-melt pressure-sensitive adhesive. In most preferred embodiments, the pressure-sensitive adhesive is an acrylic-based adhesive, since such adhesives have beneficial properties in terms of UV resistance, solvent and water resistance, next to high temperature and low temperature resistance. Furthermore, acrylic-based pressure-sensitive adhesives are generally regarded to have a high transparency and are regarded to be skin friendly.

In a preferred embodiment, the present invention provides a multi-layer adhesive tape according to the first aspect of the invention, wherein the adhesive layer 1 comprises a hot-melt acrylic-based pressure-sensitive adhesive.

The hot-melt acrylic-based pressure-sensitive adhesive has several properties which can help in compressing and contracting one or more scars:

a) It increases hydration of stratum corneum and thereby facilitates regulation of fibroblast production and reduction in collagen production. It results into softer and flatter scar. It allows skin to "breathe".
b) It protects the scarred tissue from bacterial invasion and prevents bacteria-induced excessive collagen production in the scar tissue.
c) It modulates the expression of growth factors, fibroblast growth factor β (FGF β) and tumor growth factor β (TGF β). TGF β stimulates fibroblasts to synthesize collagen and fibronectin. FGF β normalizes the collagen synthesis in an abnormal scar and increases the level of collagenases which breaks down the excess collagen. Balance of fibrogenesis and fibrolysis is ultimately restored.
d) It reduces itching and discomfort associated with scars.

This pressure-sensitive adhesive is, in use of the tape, in direct contact with one or more scars. The pressure-sensitive adhesive only adheres to the scars to such an extent that the position of the bottom-layer 2 is mainly fixated. Such moderate adhesion properties make the adhesive layer 1 especially skin friendly. In preferred embodiments, the pressure-sensitive adhesive furthermore has an approved cytotoxicity.

In other embodiments, polyacrylate-based, polyisobutylene-based, and/or silicone-based pressure-sensitive adhesives may be selected as material for the adhesive layer 1.

In still other embodiments, the adhesive layer 1 comprises a silicone gel and/or any other silicon film whose properties are desired for scar treatment.

In a preferred embodiment, the present invention provides a multi-layer adhesive tape according to the first aspect of the invention, wherein the adhesive layer 1 comprises a thickness between 10 µm and 500 µm, more preferably between 100 µm and 400 µm, and even more preferably between 200 µm and 300 µm. The thicknesses of the adhesive layer 1 allow a certain regulation of moisture and/or temperature around one or more scars. In addition, the thicknesses are sufficient to allow the sides of the top layer 4 which exceed the area of the bottom layer 2 to be oriented according to a sufficient large angle α with respect to a skin 5 surface, in a way that a sufficient amount of pressure can be applied to the one or more scars on the skin 5.

In a preferred embodiment, the present invention provides a multi-layer adhesive tape according to the first aspect of the invention, wherein the bottom layer 2 and/or top layer 4 comprise a plastic film comprising one or more polyolefin compounds, polyamide, polyester, nylon, polyvinylchloride and/or polyvinylidene chloride, and/or comprise a silicone film. Preferably, the films are stretchable to a sufficient extent, such that the multi-layer adhesive tape can be applied easily and correctly on the skin 5 of a user.

In preferred embodiments, the bottom layer 2 and/or top layer 4 comprise one or more polyolefin compounds, since such compounds are known to have good flexibility properties, which are desired for a close contact between the multi-layer adhesive tape and the skin of a user. In most preferred embodiments, the bottom layer 2 and/or top layer 4 comprise a polyurethane material. In preferred embodiments, the polyurethane material corresponds to a thermoplastic adhesive film based on polyurethanes. In embodiments, the polyurethane material can be processed with all established calendaring, lamination, bonding techniques and/or with welding, preferably high frequency welding. Polyurethane is most appreciated as component of the bottom layer 2 and/or top layer since polyurethane is known to show a high extent of flexibility and a good permeability of water and gas, which is beneficial for the healing process of one or more scars. Furthermore, polyurethane has good UV filtering properties and thus shields the sensitive scar tissue from UV rays. Besides, polyurethane bottom 2 and top layers 4 show a high conformability with the skin 5, such that no undesired gaps are left between the skin 5 and the tape when such tape is applied to the skin 5 of a user.

In embodiments, the bottom layer 2 comprises paper, one or more nonwovens, one or more woven materials, a tissue bandage, and/or microporous paper. In other embodiments, the bottom layer 2 comprises a silicone gel and/or any other silicon film whose properties are desired for scar treatment.

In preferred embodiments, the bottom layer 2 and/or top layer 4 are transparent. In such way, the multi-layer adhesive tape is perceived beneficially from an aesthetical point of view. In other preferred embodiments, the bottom layer 2 and/or top layer 4 are coloured. Most preferably, the bottom layer 2 and/or top layer 4 are coloured in a colour which mimics the skin colour. In such way, the visibility of one or more scars is shielded by the tape, while the tape is conceived positively since it approaches the look of a natural skin.

In a preferred embodiment, the present invention provides a multi-layer adhesive tape according to the first aspect of the invention, wherein the bottom layer 2 and/or top layer 4 comprise a thickness between 20 µm and 1100 µm.

In preferred embodiments, the bottom layer 2 comprises a thickness between 20 µm and 1000 µm, more preferably a thickness between 20 µm and 500 µm and even more preferably a thickness between 20 µm and 100 µm. The thicknesses of the bottom layer 2 allow the bottom layer 2 to follow the curvatures and/or movements of the skin 5 while the bottom layer 2 is thick enough to ensure easy handling of the layer 2.

In preferred embodiments, the top layer 4 comprises a thickness between 20 µm and 1100 µm, more preferably between 40 µm and 500 µm and even more preferably between 40 µm and 200 µm. The thicknesses of the top layer 4 allow the top layer 4 to follow the curvatures and/or movements of the skin 5 while the top layer 4 is thick enough to ensure easy handling of the layer 4.

In a preferred embodiment, the present invention provides a multi-layer adhesive tape according to the first aspect of the invention, wherein the bonding layer 3 comprises a rubber- or acrylic-based pressure-sensitive adhesive and the bonding layer 3 comprises a thickness between 5 µm and 300 µm.

Such rubber- or acrylic-based pressure-sensitive adhesive can easily be attached to the skin 5 of a user by the mere application of pressure, avoiding the need of solvent, water or heat for activation of adhesive. This both facilitates the attachment of the multi-layer adhesive tape and ameliorates a standard hygienic use of such multi-layer adhesive tape. The selection of a rubber- or acrylic-based pressure-sensitive adhesive for the adhesive layer 1 is not to be regarded as obvious by a person skilled in the art, since such person would rather select a more classical approach comprising the use of an adhesive which needs a solvent, water or heat for activation of the adhesive.

In preferred embodiments, the rubber- or acrylic-based pressure-sensitive adhesive is solvent- or water-based and/or a hot-melt pressure-sensitive adhesive. In most preferred embodiments, the pressure-sensitive adhesive is a solvent-based acrylic adhesive, since such adhesives exert a strong adhesion. A strong adhesion of the bonding layer 3 is needed to ensure adequate adherence to a skin 5 since both top layer 4 and bonding layer 3 will preferably be stretched at the application onto a skin 5. Furthermore, the strong adhesion property ensures that the bonding layer 3 adheres adequately to several types of skin 5 and that the adhesive force of the bonding layer 3 resists any memory effect of the top layer 4 following the stretching of this top layer 4.

In this way, the top layer 4 can maximally retain its stretched configuration, which is beneficial for the pressure- and temperature-effect which is exerted on the one or more scars on the skin 5.

In other embodiments, polyacrylate-based, polyisobutylene-based, and/or silicone-based pressure-sensitive adhesives may be selected as material for the bonding layer 3. In still other embodiments, the bonding layer 3 comprises cyanoacrylate.

In preferred embodiments, the bonding layer 3 comprises a thickness between 5 μm and 300 μm, more preferably between 10 μm and 200 μm and even more preferably between 20 μm and 100 μm. In preferred embodiments, the bonding layer 3 comprises one or more adhesives in a total amount of 20 g/m$^2$ to 60 g/m$^2$, more preferably of 30 g/m$^2$ to 50 g/m$^2$ and even more preferably of 35 g/m$^2$ to 45 g/m$^2$. The thicknesses of the bonding layer 3 and/or the amounts of one or more adhesives in the bonding layer 3 provide a good balance between adhesion and cohesion, and thus guarantee good adhesive properties.

In preferred embodiments, the liner 7 comprises a paper or filmic material. In preferred embodiments, the liner 7 comprises a siliconized liner 7, such as a siliconized paper, or a siliconized plastic film, such as a siliconized polyethylene terephthalate film or a siliconized polyethylene film. Such liner 7 materials are ideally suited to shield the adhesive of at least the adhesive layer 1, and preferably also the bonding layer 3, from the environment. In such way, the adhesive strength of the layers can be kept intact until application of the multi-layer adhesive tape.

In a preferred embodiment, the present invention provides a multi-layer adhesive tape according to the first aspect of the invention, wherein at least one of the top 4 and bottom layers 2 comprises one or more UV blocking agents.

In still other preferred embodiments, the adhesive layer 1 and/or bonding layer 4 comprise one or more UV blocking agents. In still other preferred embodiments, at least one of the top 4, bonding 3, bottom 2 and adhesive layers comprise one or more UV blocking agents.

In embodiments, the bottom layer 2 comprises a polyurethane material applying to EN410 standard and shows a measured UV blockage of 10% to 15%. In embodiments, a combination of the bottom layer 2 comprising a polyurethane material applying to EN410 standard and an adhesive layer 1 comprising an acrylic adhesive applied in an amount of 50 g/m$^2$ shows a measured UV blockage of 30 to 35%. In preferred embodiments, a combination of the bottom layer 2 comprising a polyurethane material applying to EN410 standard and an adhesive layer 1 comprising an hot-melt acrylic adhesive applied in an amount of 200 g/m$^2$ shows a measured UV blockage of 90% to 95%. The UV transmission and subsequently UV blockage was measured by a Varian Cary 5000 UV-VIS-NIR spectrophotometer equipped with an integrating sphere of 150 mm mark diameter DRA VARIAN 2500. This sphere can measure all transmission and reflection (diffused and direct). Light transmission properties were calculated from the measurement of the spectral values of transmittance and reflectance of the sample according to EN410 standard. The measurements were carried out under normal angle of incidence relative to the sample.

In a preferred embodiment, the present invention provides a multi-layer adhesive tape according to the first aspect of the invention, wherein the multi-layer adhesive tape is provided with one or more sealing edge tapes.

The sealing edge tapes are especially desired if the widths L' of the top layer 4 and bonding layer 3 are only a little bit larger than the widths L of the bottom layer 2 and adhesive layer 1. The sealing edge tapes are suitable to seal the edges of the top layer 4 and/or the bottom layer 2 of the multi-layer adhesive tape when the multi-layer adhesive tape is applied to a skin 5. In preferred embodiments, two sealing edge tapes, preferably with a parallel orientation towards each other, are applied to two opposing edges of the tape, in order to completely avoid the mere possibility of detachment of the multi-layer adhesive tape from a skin upon which it is applied. In other preferred embodiments, two pairs of parallel oriented sealing edge tapes are applied, wherein the two pairs are oriented substantially perpendicular towards each other and each pair is applied to two opposing edges of the multi-layer adhesive tape. In preferred embodiments, the sealing edge tapes comprise a filmic layer, which filmic layer preferably comprises polyurethane, and an adhesive-containing layer, which adhesive-containing layer comprises a rubber- or acrylic-based pressure-sensitive adhesive, preferably a solvent-based acrylic-based pressure-sensitive adhesive.

In a preferred embodiment, the present invention provides a multi-layer adhesive tape according to the first aspect of the invention, wherein i) the top layer 4 and bonding layer 3 are provided in a top assembly 12 of the multi-layer adhesive tape, the top assembly 12 further comprising a second peelable liner 9 adjacent to the bonding layer 3 and opposite to the top layer 4 and, optionally, a top protecting layer 10 adjacent to the top layer 4 and opposite to the bonding layer 3, and that ii) the bottom layer 2, adhesive layer 1, and first peelable liner 7 are provided in a bottom assembly 11 of the multi-layer adhesive tape, the bottom assembly 11 optionally further comprising a bottom protecting layer 8 adjacent to the bottom layer 2 and opposite to the adhesive layer 1.

Figure 4:
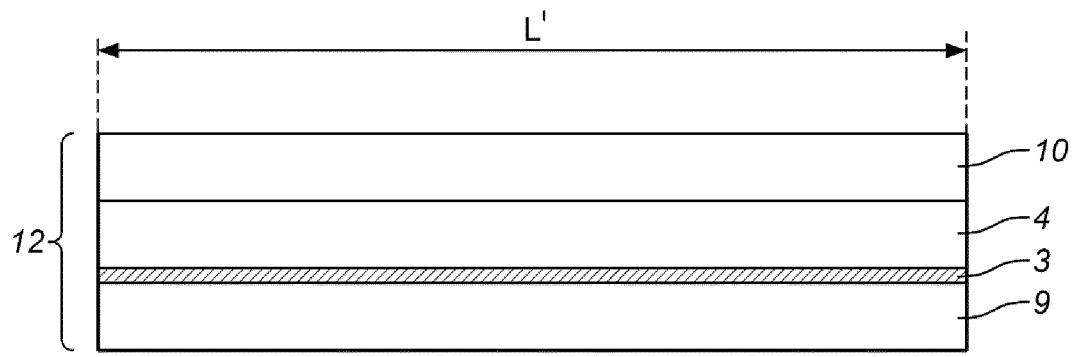
FIG. 4 is a schematic presentation of another preferred embodiment of the multi-layer adhesive tape according to the present invention.
Figure 4:
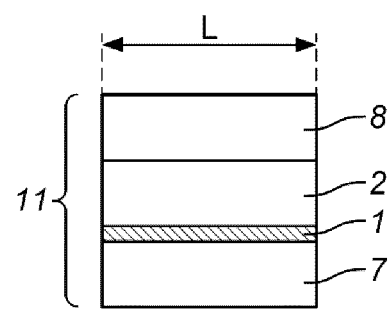

The second peelable liner 9 is intended to shield the bonding layer 3 from the environment. In this way, the adhesive properties of the bonding layer 3 are kept intact during storage of the top assembly 12. In preferred embodiments, the second peelable liner 9 comprises a paper or filmic material. In preferred embodiments, the second peelable liner 7 comprises a siliconized liner 7, such as a siliconized paper. The top protecting layer 10 is suitable for the protection of the side of the top layer 4 opposite to the bonding layer 3, during storage of the top assembly 12. In embodiments, the top protecting layer 10 comprises one or more filmic materials. The bottom protecting layer 8 is suitable for the protection of the side of the bottom layer 2 opposite to the adhesive layer 1, during storage of the bottom assembly 11. In embodiments, the bottom protecting layer 8 comprises one or more filmic materials. A schematic presentation of a preferred embodiment of the multi-layer adhesive tape according to the first aspect of the present invention, which tape is provided as a bottom assembly 11 and a top assembly 12, is shown in FIG. 4.

Providing the multi-layer adhesive tape as a combination of the top assembly 12 and the bottom assembly 11 is advantageous as it allows guidance of a user to a proper use of the tape. The bottom assembly 11 is to be used first. Therefore, both first peelable liner 7 and bottom protecting layer 8 are first removed, after which the adhesive layer 1 is applied to an area of one or more scars 6 on the skin 5. In a next step, the top assembly 12 is to be used. Therefore, both second peelable liner 9 and top protecting layer 10 are first removed, after which the bonding layer 3 is pressed to both bottom layer 2 and skin 5. In preferred embodiments, the top layer 4 and bonding layer are stretched while being applied on both skin 5 and bonding layer 3.

Generally, the multi-layer adhesive tape according to preferred embodiments of the first aspect of the invention shows excellent compression and mechanical support properties, an appropriate balance of moisture and oxygen, UV filtering properties, a desired aesthetic appearance, great waterproofing properties and an easiness of use. Furthermore, the tape can remain for seven days, in normal life conditions, and can be removed without residues.

A second aspect of the present invention provides a multi-layer adhesive tape to compress and contract a scar. The tape comprises a flexible top layer 4, a bonding layer 3, a flexible bottom layer 2 which comprises an adhesive layer 1 which is designed to cover the scar, the bottom layer 2 and the top layer 4 being bound to each other by the bonding layer 3, the top layer 4 having a width greater than that of the bottom layer 2 so as to cover it over the width of the bottom layer 2. The top layer 4 has a thickness h between 20 µm and 1100 µm, preferably between 20 µm and 900 µm, more preferably between 20 µm and 800 µm, advantageously between 20 µm and 200 µm, even more advantageously between 50 and 100 µm, so as to obtain, in the position of application of the adhesive tape on the scar, a positive pressure P which is defined by the force applied by the top layer 4 on the surface of the scar (6), in accordance with the following pressure equation:

$$P = \frac{\varepsilon \cdot E \cdot h \cdot \sin\alpha}{L}$$

where,

P corresponds to the pressure applied by the tape on the scar 6,

ε corresponds to the relative deformation of the top layer 4 and,

E represents the Young's modulus of the top layer 4, h represents the thickness of the top layer 4, L represents the width of the bottom layer 2, and the angle α is defined between one of the ends of the top layer 4 and the surface of the scar 6.

Hence, it was noted surprisingly that the selection of a thickness between 20 µm and 1100 µm, preferably between 20 µm and 900 µm, more preferably between 20 µm and 800 µm, advantageously between 20 µm and 200 µm, even more advantageously between 50 µm and 100 µm for the top layer enables a "positive" pressure to be obtained directly on and around the scar. This has the effect of mechanically compressing and contracting the scar which enables the visibility of the scar to be reduced in an unexpected way.

Using the tape according to the invention, the user simply applies the tape on the scar for a predetermined period to reduce the visibility of the scar.

Advantageously, the value of the pressure P is between 666 and 6665 Pa.

In a preferential embodiment of the tape according to the invention, the top layer 4 has a value ε between 1 and 3%.

Preferably, the Young's modulus of the top layer is between $7 \cdot 10^6$ and $7 \cdot 10^7$ Pa.

Even more preferably, the width of the bottom layer 2 is at least 1 cm.

In addition, in an advantageous embodiment of the present invention, the sine of α is between 0 and 1, preferably between 0.87 and 1.

Advantageously, the bottom layer has a thickness between 20 µm and 1000 µm. In embodiments, the bottom layer can have a thickness up to 5000 µm.

In a particular embodiment, the adhesive layer has a thickness between 10 µm and 500 µm.

Preferably, the bonding layer has a thickness between 5 µm and 300 µm.

Advantageously, the top layer and the bottom layer each comprise a polymer, such as polyurethane, polyvinyl chloride or a polyolefin, preferably a polyethylene, a polyester or a polypropylene.

In a particularly advantageous embodiment of the device according to the invention, the bottom layer comprises a UV absorber.

Particularly advantageously, the top layer has a length greater than that of the bottom layer so as to cover the latter over its entire length.

In addition, in a particular embodiment the bonding layer designed to bind together the top layer and the bottom layer comprises a pressure-sensitive polymer enabling maintaining of the film on the skin and of the positive pressure during the period of application on said skin. In addition, the pressure-sensitive polymer is also preferably adapted to contact with the skin and to the cytotoxicity criterion.

Preferably, the adhesive layer designed to cover the scar comprises a pressure-sensitive polymer which smoothes the scar. Preferably, the pressure-sensitive polymer performing a smoothing function may be a thermoplastic polymer, preferably Nolax M11.228®. In addition, the pressure-sensitive polymer performing a smoothing function is also preferably adapted to contact with the skin and to the cytotoxicity criterion.

In an embodiment, the adhesive layer 1 arranged to cover the scar includes an acrylic polymer sensitive to pressure, such as Nolax M11.1212®.

In a preferred embodiment, the bonding layer 3 arranged to mutually connect the top layer 4 and the bottom layer 2 comprises a thermoplastic polymer, such as Nolax S21.2019 PE40®.

In a preferred embodiment, the tape of the invention has a breaking load value of greater than 5 N, preferably greater than 10 N, more preferably greater than 15 N, determined for an elongation of 500%.

Other characteristics, details and advantages of the invention will be seen in the description of examples given below, on a non-limitative basis, and when referring to the appended drawings.

EXAMPLES

Example 1

TABLE 1

Embodiments of the multi-layer adhesive tape according to the first aspect of the present invention, comprising specific compositions of the composing layers

| | Example 1 | Example 2 | Example 3 | Example 4 | Example 5 |
|---|---|---|---|---|---|
| Top layer 4 | Transparent polyurethane layer; 50 g/m$^2$; layer thickness of 42 μm | Transparent polyethylene layer; 75 g/m$^2$ | Coloured polyurethane layer; 50 g/m$^2$ | Transparent polyvinylchloride; layer thickness of 40 μm | Silicon film |
| Bonding layer 3 | Solvent-based acrylic-based pressure-sensitive adhesive; 40 g/m$^2$; 40 μm | Water-based acrylic-based pressure-sensitive adhesive; 40 g/m$^2$ | Hot-melt acrylic-based adhesive; 40 g/m$^2$ | Cyanoacrylate | Cyanoacrylate |
| Bottom layer 2 | Transparent polyurethane layer comprising UV blocking agents; layer thickness of 42 μm | Nonwoven tissue | Microporous paper | Bandage | Transparent or coloured polyethylene film; layer thickness of 50 μm |
| Adhesive layer 1 | Hot-melt acrylic-based adhesive; 200 to 250 g/m$^2$; 200 to 250 μm | Silicon gel | Silicon film | Hot-melt acrylic-based adhesive; 200 to 250 g/m$^2$; 200 to 250 μm | Hot-melt acrylic-based adhesive; 200 to 250 g/m$^2$; 200 to 250 μm |
| Liner 7 | Siliconized paper | Siliconized polyethylene terephthalate | Siliconized polyethylene | Siliconized paper | Siliconized paper |

A most preferred embodiment of the first aspect of the present invention comprises a multi-layer adhesive tape according to the structure shown in FIG. 3. In the Table 1 presented above, different embodiments are provided with specific compositions of the multi-layer adhesive tape layers. Such tapes show excellent compression and mechanical support properties, an appropriate balance of moisture and oxygen, great UV filtering properties, a desired aesthetic appearance, great waterproofing properties and an easiness of use. Furthermore, the tapes can remain for seven days, in normal life conditions, and can be removed without residues.

Example 2

Figure 2:
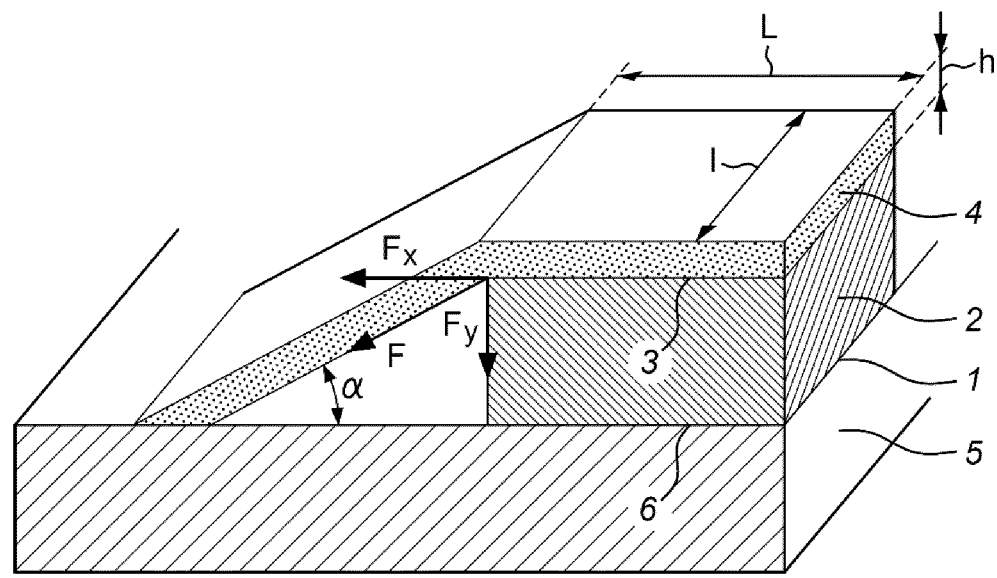
FIG. 2 is a perspective view of the multi-layer tape according to the invention.

FIG. 1 illustrates the structure of the multi-layer tape according to the invention. FIG. 2 is a perspective view of the multi-layer tape according to the invention.

As illustrated in FIG. 1, the multi-layer tape advantageously comprises four layers: a top layer 4, a bonding layer 3, a bottom layer 2 and an adhesive layer 1.

The tape according to the second aspect of the present invention may advantageously comprise a peelable covering (not illustrated on FIG. 1) to cover the tape before use.

Thus, the user will be able to remove the peelable covering and apply the tape on the closed scar. In this way, the mechanical compression and contraction referred to above can take place, resulting in a "positive" pressure being created directly on the scar. Thus, it was noted that the positive pressure is preferably between 666 Pa and 6665 Pa.

The pressure was measured using the following method of measurement:
subcutaneous insertion of a catheter filled with saline solution,
purging of the catheter and connection of the catheter to a purged tube connected to a pressure sensor (Edwards Lifesciences) and to a Drager Infinity C500 monitoring system,
application of the tape on the skin and reading of the pressure recorded.

FIG. 2 represents a variant of the tape according to the invention. As illustrated, the tape comprises the four layers indicated in FIG. 1. FIG. 2 also represents a user's skin and a scar 6 on which the tape according to the invention is applied.

The following pressure equation can be used to characterise the top layer 4:

$$P = \frac{\varepsilon \cdot E \cdot h \cdot \sin\alpha}{L}$$

where, when the tape is applied on the scar,
P has a value between 666 Pa and 6665 Pa corresponding to the force applied by the top layer 4 on the scar 6,
ε corresponds to the relative deformation of the top layer 4 and advantageously has a value between 1 and 3%, E represents the Young's modulus of the top layer which is preferably between 7.106 and 7.107 Pa, h represents the thickness of the top layer, L represents the width of the bottom layer which is advantageously at least 1 cm, and the angle α is defined between the top layer 4 and the surface of the skin 5.

Preferably, the sine a is between 0 and 1, preferably between 0.87 and 1.

The Young's modulus was determined by measuring beforehand the tensile strength of the top layer 4 as per standard ASTM D 882 and by the following equation:

$$F = E \cdot S \cdot D$$

where,

F is a force (N),

E is the Young's modulus to be determined (Pa),

S=surface area of the test specimen ($m^2$), and

D=deformation (preferably equal to 10%).

Example 3

A multi-layer adhesive tape according to the invention successively comprises a flexible top layer 4 made of polyurethane, a bonding layer comprising an acrylic-based adhesive 3, a compliant bottom layer 2 made of polyurethane and an adhesive layer 1, which comprises an pressure-sensitive acrylic polymer, such as the commercial product Nolax M 11.228®.

The sum of the thicknesses of the flexible bottom layer 2 (thickness of 42-45 μm) and the adhesive layer 1 (thickness of from 175-178 μm) is equal to 220 μm, and the sum of the thicknesses of the top layer 4 (thickness of 53-58 μm) and the bonding layer 3 (thickness of 40-45 μm) is equal to 98 μm.

A series of tests were performed by changing the total thickness corresponding to the sum of the thicknesses of the flexible bottom layer 2 and the adhesive layer 1, while maintaining the overall thickness corresponding to the sum of the thicknesses of the top layer 4 and bonding layer 3 constant to highlight the measured pressures.

These results are shown in Table 2 below.

TABLE 2

Test results of applying different tapes on a scar

| Combined thickness of bottom layer 2 and adhesive layer 1 (μm) | Combined thickness of top layer 4 and bonding layer 3 (μm) | Pressure (mmHg) | Contraction |
|---|---|---|---|
| 220 | 98 | 22 | Observed |
| 440 | 98 | 18 | Observed |
| 660 | 98 | 28 | Observed |
| 880 | 98 | 24 | Observed |
| 1100 | 98 | 33 | Observed |
| 4000 | 98 | 76 | Observed |

As illustrated in Table 2 above, increasing the combined thickness of the bottom layer 2 and adhesive layer 1 with respect to the combined thickness of the top layer 4 and bonding layer 3 leads to an increase in pressure, induced by the application of the tape on the scar to treat.

It has thus been observed that the multi-layer tape according to the present invention makes it possible to apply a contraction over the scar and also a compression of the scar. The contraction was reflected in the convergence of the banks of the scar towards the center of the scar when the tape was in the application position. This can significantly increase the healing process.

The pressure values were measured according to the pressure measurement protocol described above.

Example 4

A multi-layer adhesive tape successively comprises a flexible top layer made of polyurethane, a bonding layer comprising an acrylic-based adhesive, a flexible bottom layer made of polyethylene terephthalate having a thickness of 12 microns.

The sum of the thicknesses of the top layer (thickness of 53-58 μm) and the adhesive (thickness of 40-45 μm) is equal to 98 μm.

The multilayer tape was applied to a scar and a pressure of 0 mmHg was measured according to the measurement protocol described above. Contraction of the scar was not observed.

Comparative Example 1

A multi-layer adhesive tape successively comprises a flexible top layer made of polyurethane and a bonding layer comprising an acrylic-based adhesive.

The sum of the thicknesses of the top layer (thickness of 53-58 μm) and the adhesive (thickness of 40-45 μm) is equal to 98 μm.

The pressure was measured after application of the tape on a scar, by applying the pressure measurement protocol described above and is equal to 0 mm Hg. There is no observed contraction.

Healing time observed is also longer with the multi-layer tape of Comparative Example 1, in contrast to the multi-layer adhesive tape according to second aspect of the present invention.

Comparative Example 2

A multi-layer adhesive tape successively comprises a flexible top layer made of polyurethane, a bonding layer comprising an acrylic-based adhesive, a flexible bottom layer made of polyethylene terephthalate having a thickness of 12 microns.

The sum of the thicknesses of the top layer (thickness of 53-58 μm) and the adhesive (thickness of 40-45 μm) is equal to 98 μm.

The multi-layer tape was applied to a scar and a pressure of 0 mmHg was measured according to the pressure measurement protocol described above. The contraction of the scar was not observed.

Comparative Example 3

Table 3 listed below shows five products available on the market for which a pressure measurement has been performed in accordance to the pressure measurement protocol described above.

TABLE 3

Test results of applying different tapes on a scar

| Products | Pressure (mmHg) |
| --- | --- |
| CICA-CARE | 0-1 |
| Dermatix | 0-1 |
| Hansaplast | 0 |
| Mepitac | 0 |
| Sparadrap | 0 |

The product called Cica-Care is available from the firm Smith & Nephew® and is intended to treat scars. It is in the form of a monolayer consisting of an adhesive plate of silicone gel. The face of the adhesive layer is that which comes into contact with the skin of the scar to be treated.

The company Dermatix provides a silicone gel to be applied on a scar to be treated.

A scar reducer is also sold by the company Hansaplast and it is in the form of a polyurethane monolayer.

The so-called dressing Mepitac® provided by the company Molnlycke SA includes an upper film provided on one of its faces with a layer of silicone. According to this company, the dressing is intended for fixation of medical devices to the skin while providing a reduction in trauma to the skin.

The tape Sparadrap was also tested to measure the pressure applied to a scar.

As illustrated in Table 3 above, the tests that were carried out have made it possible to demonstrate that the products currently available on the market to treat scars do not allow to achieve sufficient contraction of the scar. In addition, the recorded pressure approaches each time about 0 mm Hg.

Naturally, this invention is in no way limited to the embodiments described above and many modifications may be made to it without departing from the framework of the appended claims.

The invention claimed is:

1. A multi-layer adhesive tape to compress and contract a scar, said multi-layer adhesive tape comprising:
    a flexible top layer,
    a bonding layer,
    a flexible bottom layer which comprises an adhesive layer to cover the scar, said flexible bottom layer and said flexible top layer being bound to each other by said bonding layer,
    wherein said flexible top layer has a width greater than a width of said flexible bottom layer so as to cover an entire width of said flexible bottom layer,
    wherein said flexible top layer has a thickness of between 20 μm and 1100 μm, and is configured to achieve, upon application of the multi-layer adhesive tape on the scar, a positive pressure P defined by the force applied by the flexible top layer on a surface of the scar, in accordance with the following pressure equation:

$$P = \frac{\varepsilon \cdot E \cdot h \cdot \sin\alpha}{L}$$

where,
P corresponds to the pressure applied by the multi-layer adhesive tape on the scar,
ε corresponds to the relative deformation of the flexible top layer and,
E represents the Young's modulus of the flexible top layer,
h represents the thickness of the flexible top layer,
L represents the width of the flexible bottom layer, and the angle α is defined between one of the ends of the flexible top layer and the surface of the scar.

2. The multi-layer adhesive tape according to claim 1, wherein a value of the pressure P is between 666 Pa and 6665 Pa.

3. The multi-layer adhesive tape according to claim 1, wherein the flexible top layer has a value ε between 1% and 3%.

4. The multi-layer adhesive tape according to claim 1, wherein the Young's modulus of the flexible top layer is between $7 \cdot 10^6$ Pa and $7 \cdot 10^7$ Pa.

5. The multi-layer adhesive tape according to claim 1, wherein the width of the flexible bottom layer is at least 1 cm.

6. The multi-layer adhesive tape according to claim 1, wherein the sine of α is between 0 and 1.

7. The multi-layer adhesive tape according to claim 1, wherein the flexible bottom layer has a thickness between 20 μm and 1000 μm.

8. The multi-layer adhesive tape according to claim 1, wherein the adhesive layer has a thickness between 10 μm and 500 μm.

9. The multi-layer adhesive tape according to claim 1, wherein the bonding layer has a thickness between 5 μm and 300 μm.

10. The multi-layer adhesive tape according to claim 1, wherein the flexible top layer and the flexible bottom layer each comprise a polymer such as polyurethane, polyvinyl chloride or a polyolefin.

11. The multi-layer adhesive tape according to claim 1, wherein the flexible bottom layer comprises a UV absorber.

12. The multi-layer adhesive tape according to claim 1, wherein the bonding layer comprises a pressure-sensitive polymer configured to allow the multi-layer adhesive tape to be maintained on the skin with a positive pressure during the period of application on the skin.

13. The multi-layer adhesive tape according to claim 1, wherein the adhesive layer comprises a pressure-sensitive thermoplastic polymer.

14. The multi-layer adhesive tape according to claim 1, wherein the adhesive layer includes an acrylic polymer sensitive to pressure.

15. The multi-layer adhesive tape according to claim 1, wherein the bonding layer comprises a thermoplastic polymer.

16. The multi-layer adhesive tape according to claim 1, wherein the multi-layer adhesive tape has a breaking load value of greater than 5 N determined for an elongation of 500%.

17. A multi-layer adhesive tape to compress and contract one or more scars, comprising:
    a top layer;
    a bonding layer adjoining said top layer;
    a flexible bottom layer adjoining said bonding layer and opposite to said top layer;
    an adhesive layer adjoining said flexible bottom layer and opposite to said bonding layer; and
    a peelable liner adjoining said adhesive layer and opposite to said flexible bottom layer,
    wherein each of said top layer and said bonding layer has a width larger than a width of each of said flexible bottom layer and said adhesive layer,
    wherein said adhesive layer comprises a rubber- or acrylic-based pressure-sensitive adhesive, and
    wherein said flexible bottom layer and/or said top layer has a thickness between 20 μm and 1100 μm.

18. The multi-layer adhesive tape according to claim 17, wherein said adhesive layer comprises a hot-melt acrylic-based pressure-sensitive adhesive.

19. The multi-layer adhesive tape according to claim 17, wherein said adhesive layer comprises a thickness between 10 µm and 500 µm.

20. The multi-layer adhesive tape according to claim 17, wherein said flexible bottom layer and/or said top layer comprises a plastic film comprising one or more polyolefin compounds, polyamide, polyester, nylon, polyvinylchloride, polyvinylidene chloride, and/or a silicone film.

21. The multi-layer adhesive tape according to claim 17, wherein said bonding layer comprises a rubber- or acrylic-based pressure-sensitive adhesive, and said bonding layer comprises a thickness between 5 µm and 300 µm.

22. The multi-layer adhesive tape according to claim 17, wherein at least one of said top layer and said flexible bottom layer comprises one or more UV blocking agents.

23. The multi-layer adhesive tape according to claim 17, further comprising one or more sealing edge tapes.

24. A multi-layer adhesive tape to compress and contract one or more scars, comprising:
    a top layer;
    a bonding layer adjoining said top layer;
    a flexible bottom layer;
    an adhesive layer adjoining said flexible bottom layer and opposite to said bonding layer; and
    a first peelable liner adjoining said adhesive layer and opposite to said flexible bottom layer,
    wherein each of said top layer and said bonding layer has a width larger than a width of each of said flexible bottom layer and said adhesive layer, and wherein said adhesive layer comprises a rubber- or acrylic-based pressure-sensitive adhesive,
    wherein said top layer and said bonding layer form a top assembly of the multi-layer adhesive tape, said top assembly further comprising a second peelable liner adjoining said bonding layer and opposite to said top layer,
    wherein said flexible bottom layer, said adhesive layer, and said first peelable liner form a bottom assembly of the multi-layer adhesive tape,
    wherein said top assembly is bondable to said bottom assembly by removal of said second peelable liner such that said bonding layer adjoins said flexible bottom layer, and
    wherein said flexible bottom layer and/or said top layer has a thickness between 20 µm and 1100 µm.

* * * * *